United States Patent [19]

Hetherington

[11] Patent Number: Plant 7,252

[45] Date of Patent: Jun. 26, 1990

[54] ORCHID LAELIOCATONIA PEGGY SAN 'CYNOSURE'

[75] Inventor: Ernest Hetherington, Arcadia, Calif.

[73] Assignee: Stewart Orchids, Carpinteria, Calif.

[21] Appl. No.: 394,421

[22] Filed: Aug. 11, 1989

Related U.S. Application Data

[63] Continuation of Ser. No. 155,603, Feb. 12, 1988, abandoned.

[51] Int. Cl.[5] ..... A01H 5/00

[52] U.S. Cl. ..... Plt./68

[58] Field of Search ..... Plt. 68

*Primary Examiner*—James R. Feyrer

*Attorney, Agent, or Firm*—Howard A. Kenyon

[57] ABSTRACT

A new and distinct variety of orchid, more particularly a Laeliocatonia hybrid plant having flowers of unique and spectacular coloring with heads of flowers erectly carried on strong sprays. The new variety is distinct from syblings of its grex by its outstanding vigorous plant structure as well as extreme freedom and frequency of bloom. A primary note with this cultivar is its compactness of growth and dramatic distinction from syblings of the grex as well as superiority over others of the type.

1 Drawing Sheet

This application is a continuation of U.S. plant patent application Ser. No. 07/155,603, filed on 2/12/88, now abandoned.

The orchid of this application was discovered by the undersigned discoverer as an outstanding member of a large sibling population of the hybrid Laeliocatonia—Peggy San. The generic prefix shall be used as Lctna. Peggy San. In October 1976 Peggy San was developed in the orchid nursery of Fred A. Stewart, Inc. at San Gabriel, CA by crossing Laeliocattleya Peggy Huffman 'Carousel' HCC/AOS x Broughtonia Sanguinea 'Stevens'. The Peggy Huffman 'Carousel' was the pod parent (mother plant.) The resulting grex of Peggy San was registered by the Stewart nursery with the Orchid Hybrid Registration Committe in London England, in 1983, and published in 1981–85 Sander's Orchid Hybride List. The new orchid was registered as "Stewart cross #Lctna. Peggy San".

On Sept. 12, 1981, the new variety appeared as a single outstanding cultivar among a large population of syblings of Peggy San, all cultivated and blooming at Stewart's San Gabriel nursery. The plant of the new variety was immediately recognized as far superior inits flowering and general growth habit to all of the members of the large population of the hybrid group Peggy San. After the new variety had been observed for a period of time, its other features of superior growth, great freedom of bloom, and vigorous structure were also noted. At this time this clone was given the cultivar name of Peggy San 'Cynosure' to identify it from all others.

ASEXUAL REPRODUCTION

After its discovery in 1981 the original plant of Peggy San 'Cynosure' was placed in the laboratories of Fred A. Stewart, Inc. nursery. During the years since 1981, a large number of plants of the new cultivar have been asexually produced by the meristem tissue culture process. Portions of the meristematic cells, capable of later differentation, were taken from the plant and developed under carefully controlled sterile conditions into new individual plants. This has been an ongoing process to cultivate this exceptional variety. The population thus produced is carried under the Code No. SM-469. All asexually propagated tissue from this cultivar carries this exact code number.

All of the propagations reproduced from the original clone have been true to the original in both plant, flower, and other characteristics. A substantial cross section have been flowered. They are exactly the same as the mother clone with no signs of mutation. All plants of the new variety have continued to be readily distinguishable from both parentage and all other syblings of Lctna. Peggy San 'Cynosure' in flower quality, plant growth habit and other characteristics.

DESCRIPTION OF THE PHOTOGRAPHS

The photograph is a close-up view of flowers typical of the new variety. It shows the same flowers and also a view from a greater distance to reveal the appearance of the entire spray in its size, growth habit and general characteristics of this cultivar Peggy San 'Cynosure'.

DESCRIPTION OF THE PLANT

The plant and its flowers are illustrated in the color photographs accompanying this specification. In some respects, the plant is typical of a Laeliocatonia hybrid. However, because of the remarkable markings of this particular cultivar, combined with the great frequency and freedom of bloom, it is unique. Its shortish strap-like coriacious leaves are erectly carried of lanceolate shape. The average leaf is 12 to 14 centimeters long, two to three centimeters wide. This does not include the stem or, as is known in orchids, the bulb. The plant attains a growth on maturity of 16 to 22 centimeters. The plant develops a structure of superior and unusual vigor and resiliency in all its parts. The rhizome is short, branching into a compact plant with many flowering leads. The growth, in addition to being compact, is naturally erect, without need to support the leaves or flower stems. The strong flower sprays are borne from the axils of the growth and are of superior strength, the flowers well carried on wiry strong stems. Its flowering habit is dependable. The flowers develop from very small sheaths throughout the winter and spring season. Many plants bloom again in the summer and into the fall with 2, 3, and even more flowerings in a year being quite common. Of special value in this cultivar is its extreme vigor and resistance to disease. They have been virus and pathogen free during development, both in the original population of Peggy San and more particularly in the cultivar, 'Cynosure,' and its meristem population of the new variety. The cells have an even chromosome compliment, which is indicated by the plant growth habit and ease of propagation which is indicative of uniform cytology and freedom of aneuploid characteristics.

DESCRIPTION OF THE FLOWER

The outstanding merit of the new variety, in addition to its compactness and freedom of bloom, is the dramatic and contrasting combination of flower colors. What is especially notable is the very round shape of the flowers with each flower carried perfectly on a wiry stem well above the foliage.

The base color of these sepals and petals is delicate, medium lavender, closest to new *Royal Horticultural Society Colour Chart* (*R.H.S.C.C.*) 1986 edition as red-purple, group sheet 70, swatch C of fan number 2. (Horticultural example is Cattleya of labiata type.).

On the petals there is a heavy triangular flaring of greyed-purple, group sheet number 187, color swatch D, fan number 4 (greyed colors). The exact color of the lip is also greyed-purple, group sheet number 187, swatch D, fan number 4. On the inner side lobes of the labellum are light air brushed yellow areas. Specifically, the colors are from sheet number one, shaded from swatch B to D of fan number 1 of the yellow to orange-yellow to red group.

The flowers of the variety are larger and stronger in structure than the average grex or cultivar in this line of breeding. The flowers average 3 centimeters in petal with a petal length of 3½ centimeter average. The total span of the flowers averages 5–6 centimeters. The new variety can carry as many as 5–8 flowers on each spray on a mature well-grown plant. Additionally, because of the compactness of the plant and its freedom of bloom, a single plant can have from 2–5 sprays of flowers out at one time. Additionally on the flower description, the petals are flat and press against the three sepals for an appearance of extreme roundness. They are carried without twisting or turning or recurving. The sepals and petals are in symetrical balance to the lip and create a good, round shape to the flower as a whole. What is exceptional also about this cultivar is the uniformity of the flower quality from one blooming to the next regardless of weather conditions or temperature, lasting from 2–4 weeks on the average.

The blooming season of this cultivar is throughout the spring and well into the summer, through year round bloom may be characteristic as the population becomes mature.

The above described characteristics of the new variety make it of exceptional value in the commercial orchid plant sales market. The vigor, excellent bloom season, total reliability and freedom of bloom are characteristics which set this particular cultivar above not only syblings in the grex but other gregi in this entire line of breeding.

What is claimed is:

1. A new and distinct plant in the hybrid genus Laeliocatonia, discovered as a superior selection within the grex Laeliocatonia 'Peggy San', substantially as described and illustrated, named 'Cynosure', characterized by a combination of clearness of coloring, superior flower substance, size, and shape and further characterized by its exceptional vigor, reliability of bloom and dramatic flower qualities.

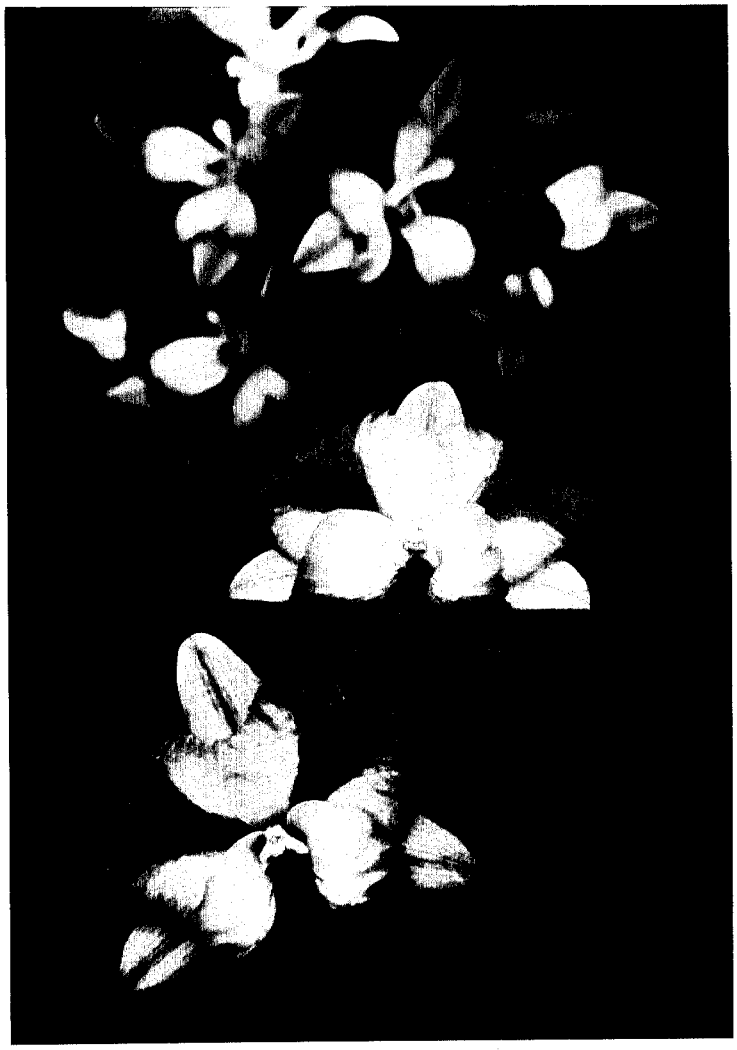

* * * * *